United States Patent [19]

Trachsler et al.

[11] 4,356,121
[45] Oct. 26, 1982

[54] PROCESS FOR THE PRODUCTION OF N-CYANOLACTAMS

[75] Inventors: Dieter Trachsler, Kaiseraugst; Friedrich Lohse, Oberwill, both of Switzerland

[73] Assignee: Ciba-Geigy Corporation, Ardsley, N.Y.

[21] Appl. No.: 305,662

[22] Filed: Sep. 25, 1981

[30] Foreign Application Priority Data

Oct. 7, 1980 [CH] Switzerland .................. 7480/80

[51] Int. Cl.³ .................................. C07D 223/10
[52] U.S. Cl. .................. 260/239.3 R; 260/239.3 B; 260/326.5 FL; 260/313.1; 260/319.1; 546/243; 546/112; 546/146; 546/153
[58] Field of Search .............. 260/239.3 R, 326.5 FL, 260/239.3 B, 313.1, 219.1; 546/243, 112, 143

[56] References Cited

FOREIGN PATENT DOCUMENTS

| | | |
|---|---|---|
| 1175678 | 8/1964 | Fed. Rep. of Germany ... 260/239.3 R |
| 1905098 | 8/1970 | Fed. Rep. of Germany ... 260/239.3 R |
| 1670851 | 2/1971 | Fed. Rep. of Germany ... 260/239.3 R |

OTHER PUBLICATIONS

CA, 73, 99400x, (1970).
CA, 60, 15835d, (1964).

Houben-Weyl—"Methoden der Organishchen Chemie", vol. VIII, 177, (1952).

*Primary Examiner*—Robert T. Bond
*Attorney, Agent, or Firm*—Luther A. R. Hall

[57] ABSTRACT

The invention provides a process for the production of N-cyanolactams of the formula I

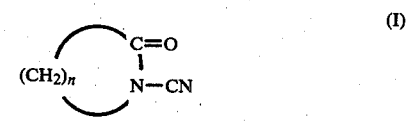

which process comprises reacting a compound of the formula II

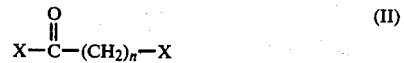

in the presence of an inorganic hydrogen halide acceptor, with cyanamide or with a salt thereof.

The N-cyanolactams obtained by the process of the invention are valuable intermediates for the production of polyadducts, or they can be used as activators in polymerization reactions.

The symbols in formulae (I) and (II) are as defined in claim 1.

7 Claims, No Drawings

PROCESS FOR THE PRODUCTION OF N-CYANOLACTAMS

The present invention relates to a novel process for the production of N-cyanolactams.

A number of processes for the production of N-cyanolactams are already known. For example, according to the teaching of German Offenlegungsschrift No. 1 670 851, lactime-O-alkyl ethers are reacted with derivatives of carbonyl chloride in the absence of a solvent or in the presence of an inert anhydrous organic solvent, to give lactam-N-carboxylic acid derivatives. Mention is made of N-cyanolactam, but there are no supporting Examples. However, an Example for the production of N-cyanocaprolactam from caprolactime-O-methyl ether and chlorine cyanide, in the presence of a solvent, is contained in German Offenlegungsschrift No. 1 905 098, which describes a process for the production of polyamides in the presence of N-substituted lactams as activators. According to the process described in German Pat. No. 1 175 678, N-cyanolactams are obtained by reacting salts of lactams, in the presence of organic solvents, with cyanogen halides.

The prior art processes give only moderate yields and some require the use of inert organic solvents.

It has now been found that N-cyanolactams are obtained in high yield by cyclising $\omega$-haloacyl halides with cyanamides or salts thereof.

Accordingly, the present invention provides a process for the production of N-cyanolactams of the formula I

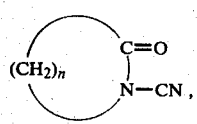

(I)

wherein n is an integer from 3 to 5 and the methylene carbon atoms are unsubstituted or substituted by one or two methyl or ethyl groups, or two adjacent methylene carbon atoms form part of a $C_5$–$C_8$ cycloaliphatic ring or a benzene ring, which process comprises reacting a compound of the formula II

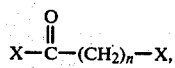

(II)

wherein n is an integer from 3 to 5, the methylene carbon atoms are unsubstituted or substituted by one or two methyl or ethyl groups, or two adjacent methylene carbon atoms form part of a $C_5$–$C_8$ cycloaliphatic ring or a benzene ring, and each of the symbols X independently is a halogen atom, in the presence of an inorganic hydrogen halide acceptor, with cyanamide or a salt thereof.

It is preferred to react 1 mole of compound of the formula II with 1 mole of cyanamide, in the presence of 2 moles of an inorganic hydrogen halide acceptor, or with 1 mole of a cyanamide salt, in the presence of 1 mole of an inorganic hydrogen halide acceptor.

Each of the symbols X in formula II can independently be chlorine, bromine or iodine, with chlorine or bromine being preferred.

Examples of suitable $C_5$–$C_8$ cycloaliphatic rings of which two adjacent methylene carbon atoms form part, are cyclopentyl, cyclohexyl or cyclooctyl.

Examples of compounds of the formula II are: $\gamma$-chlorobutyryl chloride, $\gamma$-bromobutyryl chloride, $\delta$-chlorovaleryl chloride, $\delta$-bromovaleryl chloride, $\epsilon$-chlorohexanoyl chloride, $\epsilon$-bromohexanoyl chloride, $\gamma$-chlorovaleryl chloride, 2-chloromethylbenzoyl chloride, and the corresponding bromides.

It is preferred to use compounds of the formula II which are unsubstituted and contain no rings.

The process of this invention is preferably used for the production of N-cyanopyrrolidone, N-cyanopiperidone and N-cyanocaprolactam. Cyanamide or salts thereof are employed as coreactants of the cited $\omega$-haloacyl halides of the formula II. Cyanamide can be used in solid form or as aqueous solution. Suitable cyanamide salts are salts with alkali metals and alkaline earth metals. Preferred salts are those with alkali metals, in particular with sodium and potassium. The cyanamide salts are preferably formed during the reaction when the cyanamide comes into contact with the base which acts as hydrogen halide acceptor. Suitable hydrogen halide acceptors are, for example, the hydroxides, carbonates and bicarbonates of alkali metals and alkaline earth metals. It is preferred to use an alkali metal hydroxide as hydrogen halide acceptor, in particular sodium hydroxide or potassium hydroxide.

The process is preferably carried out by adding approximately equivalent amounts of the reactants to each other at 0° to 10° C. and then heating the reaction mixture to 30° to 100° C. The reaction can be conducted in an aqueous or organic solution. Suitable organic solvents are preferably aprotic solvents such as dimethyl formamide and dimethyl acetamide. If the process is carried out in organic solution, the cyanamide is preferably employed in the form of a salt, e.g. as mono- or disodium cyanamide. A preferred process is one in which the reaction is conducted in an aqueous solution.

The N-cyanolactam of the formula I can be isolated by concentrating the solution and extracting the residue with an organic solvent. Suitable solvents are water-immiscible solvents, e.g. aromatic hydrocarbons such as toluene or xylene, halogenated aromatic hydrocarbons such as chlorobenzene, dichlorobenzene or chloronaphthalene, ethers such as diethyl ether, diisopropyl ether and di-n-butyl ether, dioxane or diphenyl ether, and esters such as n-butyl acetate.

If the process is carried out in aqueous solution, the solvent can be added after the formation of the cyanamide salt and extraction performed simultaneously with the cyclisation reaction. The crude product is purified, if desired, by means of a suitable purification method, e.g. distillation or recrystallisation.

The preferred procedure is that the corresponding amount of cyanamide is added, in solid form, to aqueous (4 N or cencentrated) sodium or potassium hydroxide which has been cooled to 0° to 10° C., whereupon the monosodium or monopotassium cyanamide is formed in the solution. To this solution is added dropwise, at 0° to 10° C., an equivalent amount (based on the cyanamide employed) of the $\omega$-haloacyl halide of the formula II, while ensuring adequate cooling, as this first reaction step, i.e. the formation of the haloacyl cyanamide salt, is strongly exothermic. The cyclisation reaction commences at 0° to 10° C. and is then brought to completion by raising the temperature. Depending on the intermediate obtained, temperatures in the range from about 30° to 40° C. suffice; but higher temperatures up to 100° C. can also be applied. The reaction course can be illustrated as follows:

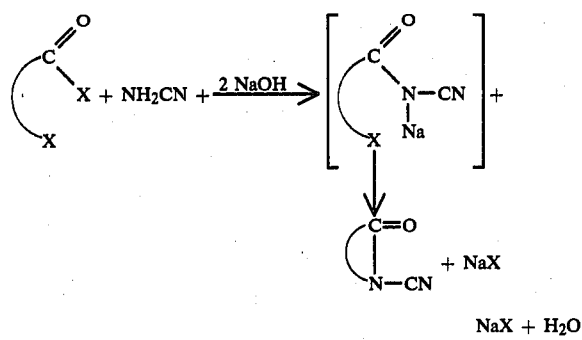

wherein X is a halogen atom.

The ω-haloacyl halides of the formula II are known compounds, most of which are commercially available or can be prepared by known methods.

The N-cyanolactams of the formula I obtained by the process of this invention are valuable intermediates, e.g. for the production of crosslinked nitrogen-containing polyadducts which are obtained by the addition of organic compounds containing at least 2 carbon atoms and at least 2 hydroxyl and/or 2 amino groups, to N-cyanolactams. They can also, however, be used direct as activators in polymerisation reactions, e.g. in the production of polypyrrolidone. They can also be used for curing epoxy resins.

The invention is illustrated by the following Examples, in which percentages are by weight.

EXAMPLE 1

80 g (2 moles) of sodium hydroxide are dissolved in 500 ml of water and the solution is cooled to 0° C. To this solution are added 42 g (1 mole) of cyanamide in portions. Then 141 g (1 mole) of γ-chlorobutyryl chloride are added dropwise, at 0°–5° C., over 2 hours to the clear, colourless cyanamide solution, while ensuring adequate cooling. When the dropwise addition is complete, the mixture is stirred for 1 hour at the same temperature. Then 1 liter of methylene chloride is added and the reaction mixture is warmed for 1 hour to reflux temperature (40° C.). The two clear, colourless phases are separated in a separating funnel. The organic phase is dried over sodium sulfate, filtered, and the solvent is removed in a water jet vacuum. Yield: 110 g (99.9% of theory). The crude product is a pale yellowish, slightly cloudy liquid.

High vacuum distillation of the crude product yields 78.2 g (71% of theory) of N-cyanopyrrolidone as a colourless, clear liquid with a boiling point of 92°–94° C./6.67 Pa. A gas chromatogram shows 95.85% of N-cyanopyrrolidone and 3.43% of an isomer.

EXAMPLE 2

59.4 g (1.484 moles) of sodium hydroxide are dissolved in 370 ml of water and the solution is cooled to 0° C. To this solution are added 13.2 g (0.742 mole) of cyanamide in portions. Then 115 g (0.742 mole) of δ-chlorovaleryl chloride are added dropwise, at 0°–8° C., over 1 hour to the clear, colourless cyanamide solution. The ensuing reaction is strongly exothermic, so that intensive cooling is necessary. When the dropwise addition is complete, the mixture is stirred for 1 hour at 0° C. Then 740 ml of methylene chloride are added and the reaction mixture is subsequently warmed for 1 hour to reflux temperature (40° C.). The two phases are separated in a separating funnel. The aqueous phase is extracted once more with 740 ml of methylene chloride. The combined organic phases are dried over sodium sulfate, filtered, and the solvent is removed in a water jet vacuum. Yield: 79.6 g (86.4% of theory). The crude product is a pale yellowish liquid which, according to gas chromatographic analysis, contains 79.95% of N-cyanopiperidone. An isomer is not detected. High vacuum distillation of the crude product yields 44 g (47.8% of theory) of N-cyanopiperidone as a pale yellowish liquid with a boiling point of 125° C./13.3 Pa. Gas chromatographic analysis shows the product to be 99.19% pure.

What is claimed is:

1. A process for the production of a N-cyanolactam of the formula

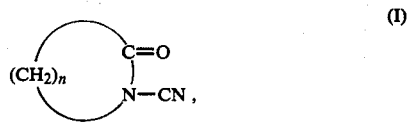

wherein n is an integer from 3 to 5 and the methylene carbon atoms are unsubstituted or substituted by one or two methyl or ethyl groups, or two adjacent methylene carbon atoms form part of a $C_5$–$C_8$ cycloaliphatic ring or a benzene ring, which process comprises reacting a compound of the formula II

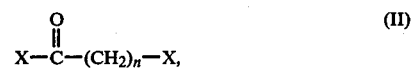

wherein n is an integer from 3 to 5, the methylene carbon atoms are unsubstituted or substituted by one or two methyl or ethyl groups, or two adjacent methylene carbon atoms form part of a $C_5$–$C_8$ cycloaliphatic ring or a benzene ring, and each of the symbols X independently is a halogen atom, in the presence of an inorganic hydrogen halide acceptor, with cyanamide or a salt thereof.

2. A process according to claim 1, wherein there is used a compound of the formula II which contains no substituents or rings.

3. A process according to claim 1, wherein 1 mole of the compound of formula II is reacted with 1 mole of cyanamide, in the presence of 2 moles of an inorganic hydrogen halide acceptor, or with 1 mole of a cyanamide salt, in the presence of 1 mole of an inorganic hydrogen halide acceptor.

4. A process according to claim 1, wherein there is used a compound of the formula II, in which each of the symbols X independently is chlorine or bromine.

5. A process according to claim 1, wherein sodium hydroxide or potassium hydroxide is used as hydrogen halide acceptor.

6. A process according to claim 1, wherein equivalent amounts of the reactants are added to each other at 0°–10° C. and the reaction mixture is subsequently heated to 30°–100° C.

7. A process according to claim 1, wherein the reaction is carried out in an aqueous solution.

* * * * *